(12) United States Patent
Bartlett et al.

(10) Patent No.: US 6,190,920 B1
(45) Date of Patent: Feb. 20, 2001

(54) METHOD FOR DETECTING ENZYME CATALYZED CYCLIZATION

(75) Inventors: Paul A. Bartlett, Oakland; Matthew T. Burger, Berkeley, both of CA (US)

(73) Assignee: The Regents of the University of California, Oakland, CA (US)

( * ) Notice: Under 35 U.S.C. 154(b), the term of this patent shall be extended for 0 days.

(21) Appl. No.: 08/967,910

(22) Filed: Nov. 12, 1997

(51) Int. Cl.$^7$ .............................. G01N 33/00; C07K 5/12
(52) U.S. Cl. .......................... 436/89; 436/86; 436/501; 435/4; 530/317
(58) Field of Search .............................. 530/317; 436/86, 436/89, 501; 435/4

(56) References Cited

U.S. PATENT DOCUMENTS

| | | | |
|---|---|---|---|
| 5,480,971 | 1/1996 | Houghten et al. | 530/328 |
| 5,504,190 | 4/1996 | Houghten et al. | 530/329 |
| 5,506,337 | 4/1996 | Summerton et al. | 528/391 |
| 5,539,083 | 7/1996 | Cook et al. | 530/333 |
| 5,541,061 | 7/1996 | Fodor et al. | 435/6 |
| 5,550,215 | 8/1996 | Holmes | 530/334 |
| 5,556,762 | 9/1996 | Pinilla et al. | 435/7.21 |
| 5,565,324 | 10/1996 | Still et al. | 435/6 |
| 5,565,325 | 10/1996 | Blake | 435/7.1 |
| 5,618,825 | 4/1997 | Baldwin et al. | 514/317 |

OTHER PUBLICATIONS

Domingo et al., Int. J. Pept. Prot. Res. vol. 46, pp. 79–87, 1995.*

Webster's II New Riverside Dictionary, p. 871, 1984.*

Brummel C.L. et al., "A Mass Spectrometric Solution to the Address Problem of Combinatorial Libraries," Science, vol. 264:399–402 (1994).

Erb et al., "Recursive deconvolution of Combinatorial Chemical Libraries," Proc. Nat. Acad. Sci., USA, vol. 91:11422–11426 (1994).

Holmes, C.P.; Jones, D.G., "Reagents for Combinatorial Organic Synthesis: Development of a New o–Nitrobenzyl Photolabile Linker for Solid Phase Synthesis," J. Org. Chem., vol. 60:2318–2319 (1995).

Lowe Gordon, "Combinatorial Chemistry," Chemical Society Reviews, pp. 309–317 (1995).

Ohlymer et al., "Complex Synthetic Chemical Libraries Indexed with Molecular Tags," Proc. Nat. Acad. Sci., USA, vol. 90:10922–10926 (1993).

Thompson et al., "Synthesis and Applications of Small Molecule Libraries," Chem. Rev., vol. 96:555–600 (1996).

Terrett et al., Tetrahedron Report No. 377, "Combinatorial Synthesis–The Design of Compound Libraries and Their Application to Drug Discovery," Tetrahedron, vol. 51:8135–8173 (1995).

* cited by examiner

Primary Examiner—Bennett Celsa
(74) Attorney, Agent, or Firm—Cooley Godward LLP

(57) ABSTRACT

A method for detecting cyclization of acyclic compounds is disclosed. In particular, the invention relates to a method of screening for macrocyclic peptidase inhibitors, and is useful for screening a combinatorial library of compounds.

20 Claims, No Drawings

METHOD FOR DETECTING ENZYME CATALYZED CYCLIZATION

This invention was made with Government support under Grant (Contract) No. GM-30759 awarded by the National Institutes of Health. The Government has certain rights to this invention.

INTRODUCTION

1. Technical Field

The invention relates to a method for detecting cyclization of acyclic compounds. In particular, the invention relates to a method of screening for macrocyclic peptidase inhibitors, and is especially useful for screening a combinatorial library of compounds.

2. Background

Recently there has been much interest in using combinatorial techniques for preparing libraries of organic compounds, including peptides, oligonucleotides, and the like. See, for example, U.S. Pat. Nos. 5,480,971, 5,506,337, 5,504,190, 5,539,083, 5,541,061, 5,550,215, 5,556,762, 5,565,324, 5,565,325, and 5,618,825. One advantage of such an approach is that initially a large number of compounds can be prepared in small quantities, and the compounds thus produced screened in order to discover ligands having useful activity. Those compounds found to exhibit useful activity may then be prepared on a larger scale by conventional techniques for further testing. Additionally, once a preferred compound has been identified from the initial screening, other combinatorial libraries of compounds closely related to the initially selected compound may be assembled using the same combinatorial techniques. In this fashion, a rapid and efficient method is employed for identifying active compounds.

An area of increasing interest relates to macrocyclic peptidase inhibitors. Such inhibitors are useful as antihypertensives, HIV protease inhibitors, thrombin inhibitors, etc. Because it requires enormous effort to make complex macrocyclic analogs by conventional synthetic techniques, the ability to identify those ring systems useful as macrocyclic peptidase inhibitors before undertaking such a synthetic effort would be desirable. Thus, the preparation of a combinatorial library of compounds coupled with a rapid and convenient method for identifying the components of that library that are useful as macrocyclic peptidase inhibitors would be especially valuable.

A method of determining the potential of compounds for utility as macrocyclic peptidase inhibitors has been discovered. This invention is based upon the observation that a ring system that is favorably bound as an inhibitor can be generated from a linear molecule by action of the target enzyme. Linear molecules are easier to synthesize than macrocycles, and therefore a method for identifying acyclic compounds that are cyclized readily by a target enzyme has utility for discovering macrocyclic peptidase inhibitors. The method is particularly useful for the screening of a large number of acyclic compounds generated in a combinatorial library for utility as macrocyclic peptidase inhibitors.

Relevant Literature

A review of combinatorial techniques is given in "Combinatorial Chemistry" by Gordon Lowe, *Chemical Society Reviews*, 1995, pp 309–317.

SUMMARY OF THE INVENTION

The present invention concerns a method for detecting enzyme-catalyzed cyclization of acyclic amino compounds, comprising;

a) contacting a peptidase with an acyclic amino compound of Formula I:

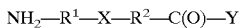

wherein:
C(O)Y represents a carboxylic acid, ester, or amide derivative capable of acylating or being hydrolyzed by a peptidase;
$R^1$ and $R^2$ each represent a series of subunits connected by covalent bonds, in which
   one of said subunits in $R^1$ is linked to a dye molecule or a resin;
   one of said subunits in $R^2$ is linked to a dye molecule or to a resin; and
X is a group cleavable under reaction conditions that do not cleave an amide;
with the proviso that the acyclic amino compound contains only one dye molecule and one resin-linked subunit;
b) contacting the product of step a) with an agent capable of cleaving subunit X under reaction conditions that do not cleave an amide; and
c) isolating the resin;
wherein cyclization of said acyclic amino compound is detected by retention of said dye on the resin.

Preferred is where Y is $-OR^3$, $-SR^3$, or $-NHR^3$, in which;
$R^3$ is hydrogen, alkyl, cycloalkyl, aryl, or heteroaryl; and
$R^1$ and $R^2$ each represent a series of 1–20 subunits, wherein the number of subunits represented by $R^1$ and $R^2$ combined represent between 2 and 30 subunits.

Another aspect of the invention relates to a method of discovering effective peptidase inhibitors, comprising:
a) contacting an acyclic amino compound of Formula I with a peptidase;
b) contacting the product of step a) with an agent capable of cleaving group X under reaction conditions that do not cleave an amide; and
c) isolating the resin;
wherein the presence of an effective peptidase inhibitor is indicated by retention of said dye on the resin, and the effective peptidase inhibitor is a compound of Formula II:

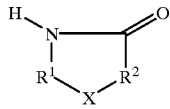

where $R^1$, $R^2$, and X are as defined above.

DESCRIPTION OF SPECIFIC EMBODIMENTS

As used herein:

"Alkyl" means a branched or unbranched saturated monovalent hydrocarbon radical containing 1 to 12 carbon atoms, such as methyl, ethyl, n-propyl, isopropyl, n-butyl, sec-butyl, tert-butyl, n-hexyl, 2-methylhexyl, n-octyl, 4-ethyloctyl, n-decyl, n-dodecyl, and the like.

"Lower alkyl" means a branched or unbranched saturated monovalent hydrocarbon radical containing 1 to 6 carbon atoms, such as methyl, ethyl, propyl, isopropyl, tert-butyl, butyl, n-hexyl and the like.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Lower alkoxy" means the group —O—(lower alkyl) wherein lower alkyl is as herein defined.

"Halo" or "halogen" means fluoro, chloro, bromo, or iodo.

"Alkylene" means a branched or unbranched saturated divalent hydrocarbon radical containing 1 to 12 carbon atoms, such as methylene, ethylene, 1,2-propylene, 1,4-butylene, 1,3-butylene, 1,5-pentylene, 1,3-pentylene, 1,6-hexylene, 1,12-docecylene, and the like. "Optionally substituted alkylene" means alkylene as defined optionally mono-, di- or tri-substituted, independently, with lower alkyl, lower alkoxy, halo, nitro, trifluoromethyl and/or cyano, such as difluoromethylene. The alkylene chain is optionally interrupted by a heteroatom chosen from oxygen, sulfur, and nitrogen, "Alkenylene" means a branched or unbranched unsaturated divalent hydrocarbon radical containing 2 to 12 carbon atoms, such as ethene, 1-propene, 1-butene, 3-methylbut-1-ene, 1-pentene, 2-methylpent-1-ene, 1-hexene, 1-docecene, and the like.

The term "aryl" refers to a monovalent unsaturated aromatic carbocyclic radical having a single ring (e.g., phenyl) or two rings (e.g., naphthyl, biphenyl, indanyl, 1,2,3,4-tetrahydronaphthyl, benzocycloheptane), which can optionally be mono-, di- or tri-substituted, independently, with OH, COOH, lower alkyl, lower alkoxy, halo, nitro, amino, alkylamino, dialkylamino, trifluoromethyl and/or cyano.

The term "heteroaryl" refers to a monovalent aromatic carbocyclic radical having 1–3 heteroatoms within one or two rings, (e.g., thiophenyl, furanyl, pyridyl, thiazolyl, pyrimidine, oxazolyl, benzoxazole, benzofuran, benzothiophene, indolinyl, quinoline), which can optionally be mono-, di- or tri-substituted, independently, with OH, COOH, lower alkyl, lower alkoxy, halo, nitro, amino, alkylamino, dialkylamino, trifluoromethyl and/or cyano.

The term "peptidase" refers to the class of enzymes that are capable of hydrolyzing the amide linkage such as that between amino acids in an oligopeptide or polypeptide.

The term "dye" or "dye molecule" refers to an entity that might be visible under UV light or via fluorescence, but preferably can be seen in the visible spectrum. Examples of such dyes are analogs of Disperse Red 1, xylenol orange, malachite green, Coomassie blue, dabsyl or dabcyl derivatives, fluoroscein, and the like. They may be attached to one of the subunits comprising $R^1$ and $R^2$ by any means; the attachment must be stable to conditions used for the cleavage of X. Examples include, but are not limited to, attachment of an alkyl, aryl, sulfonyl, or acyl group to a nitrogen atom of a subunit; attachment of an alkyl or aryl group to an oxygen or sulfur atom of a subunit; and direct attachment of an alkyl or aryl group to the carbon framework of a subunit. For example, disperse red can be attached to a subunit using the ethylamino sidechain by conventional means. Similarly, xylenol orange can be attached to a subunit via its carboxy sidechain (to form an amide), Coomassie blue via its phenolic group (to form an ether), the dabsyl group through a sulfonyl group, the dabcyl group through a carboxyamide, fluoroscein through a thiourea linkage, and malachite green can be attached directly through the unsubstituted phenyl group.

The term "resin" refers to the polymer support materials used for solid phase synthesis, such as crosslinked polystyrene ("Merrifield resin"), Kieselguhr (silica gel), polyacrylamide, or such polymers derivatized with poly(ethylene glycol), e.g., TentaGel (polystyrene functionalized with poly(ethylene glycol) and terminated with a haloalkyl group), or PEGA resins.

$R^1$ and $R^2$ are each defined as a series of subunits linked together by covalent bonds. For the purpose of this invention, any subunit known to organic chemists that can be linked together covalently is functional. The term "subunit" includes moieties such as amino acids, which could then be linked conventionally by the formation of amide bonds. Similarly, hydroxy acids could be linked as esters, or linked to amino derivatives as amides. Other moieties included in, but not limited to, the term "subunit(s)" are optionally substituted alkylene, optionally substituted alkenylene, optionally substituted aryl, optionally substituted arylalkyl, optionally substituted heteroaryl and optionally substituted heteroarylalkyl.

The method of the present invention is operable regardless of the number of subunits defined by $R^1$ and $R^2$. However, it is preferred that $R^1$ and $R^2$ each represents a series of 1–100 subunits, and more preferred that $R^1$ and $R^2$ each represents a series of 1–20 subunits, wherein the number of subunits represented by $R^1$ and $R^2$ combined represent between 6 and 40 subunits.

The term "amino acids" is intended to include all those amino acids that are capable of being linked together or alternatively linked to other subunits as defined above that are not amino acids. The term includes both those amino acids specified by the genetic code as well as alpha-amino acids that must be prepared synthetically, beta-amino acids, and longer amino acids. The amino acids are not limited to those with the natural L stereochemistry. Examples of other amino acids include piperidine-4-carboxylic acid, 3-(aminomethyl)benzoic acid, beta-alanine, 4-aminobutanoic acid, homophenylalanine, 1-aminocyclopentane carboxylic acid, and the like.

In general, it is intended that the subunits defined by $R^1$ and $R^2$ are divalent, and are linked by covalent bonds in a sequential fashion, i.e. in a manner such that a ring (if formed) would be a 6–40 membered ring plus X and the newly formed amide bond. However, it should be understood that subunits could also be attached in a monovalent fashion to the ring-forming subunits, i.e. as a monovalent substituent on the ring.

In the claims, X is defined as a bridging moiety that is cleavable under reaction conditions that do not cleave an amide under the conditions used to cleave X. Such bridging moieties include, but are not limited to, an ester linkage (cleaved by selective treatment with a base), a disulfide linkage (cleaved by reduction), a —CH(OH)—CH(OH)— linkage (cleaved by oxidation), a carbonate linkage (cleaved by selective treatment with a base), and the like.

METHODS OF PREPARATION

Provided by the present invention is a simple assay for cyclization that can be utilized for the discovery of peptidase inhibitors. In its broadest aspect, as depicted in Reaction Scheme I, the invention relates to an acyclic amino compound of formula (1), in which $R^1$ and $R^2$ each represent a series of 1–20 subunits connected by covalent bonds, in which one of the subunits that constitute $R^1$ is attached to a dye molecule and one of the subunits that constitute $R^2$ is attached to a resin. Reaction Scheme I illustrates the dye attached to one of the $R^1$ constituents and the resin is attached to one of the $R^2$ constituents, but the method works equally well if this is reversed. The only requirement of the method is that the dye and the resin are situated on opposite sides of the cleavable subunit X.

REACTION SCHEME I

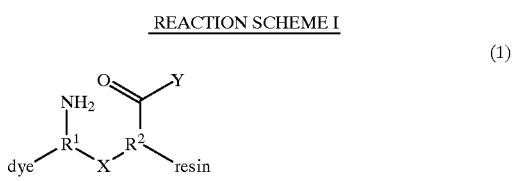

(1)

X is a group that is cleavable under reaction conditions that do not cleave an amide, and Y is any group that is capable of displacement to form an amide in the presence of a peptidase, for example hydroxy, alkoxy, aryloxy, amido, and the like.

As shown in Reaction Scheme II, it is evident that after contact with a peptidase there are two possible consequences, the first being that the acyclic compound has cyclized to form a cyclic amide of formula (2), or it has not cyclized and either remains unchanged as (1) or alternatively, if Y is not hydroxy, it has been hydrolyzed to the free acid (i.e. where Y is OH).

REACTION SCHEME II

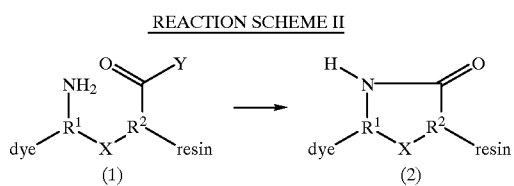

The group X is then cleaved under suitable reaction conditions. For example, if X represents an ester bond, reaction with a base under suitable conditions will cleave the ester without cleaving any amide moiety present. The dye is chosen so that it is also unaffected by the cleavage reaction conditions.

It can be seen that cleavage of the product of Reaction Scheme II will give different results, depending upon whether a compound of formula (1) or (2) had been formed, as shown in Reaction Scheme III.

REACTION SCHEME III

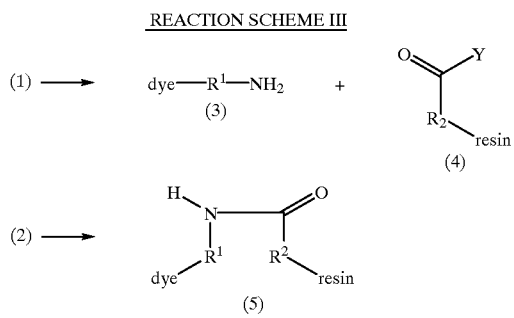

The compound of formula (3) is soluble; the compounds of formula (4) and (5) are not, as a consequence of their attachment to a resin. Therefore, whether or not cyclization has taken place, a solid insoluble product will remain, which can be filtered off and purified by washing. However, if cyclization has taken place and a product of formula (5) has been formed, the dye will still be attached to the resin, which consequently is visibly colored, or is visible under UV or by fluorescence, depending upon the dye used. If cyclization has not taken place and products of formula (3) and (4) have been formed, the dye will be seen in the filtrate and the insoluble resin material will be colorless.

As a consequence, a dependable method of determining whether cyclization has taken place is disclosed. Retention of the dye in the resinous material unambiguously demonstrates cyclization of the amino compound, which in turn, as noted above, determines that the cyclized compound (absent the dye and resin) is potentially useful as a macrocyclic peptidase inhibitor. One advantage of this method is that it is highly suited to the use of combinatorial techniques for the preparation and screening of a library of compounds. The library is assembled by conventional techniques on a resin and screened by the method of the invention. The assay can identify individual beads from an encoded library and thus take full advantage of the combinatorial approach.

An example of the assembly of a combinatorial library is as follows: using conventional techniques, a resin to which an amino group is attached, for example PEGA (polyethyleneglycol-polyacrylamide) beads, is reacted with the mono ester of glutaric acid, the ester hydrolyzed to the free acid, and the resin beads bearing the acid divided into portions. The protecting ester group (preferably allyl) is removed from the amino acid of each portion, and the carboxylic acid thus formed is coupled with an a-amino acid (for example, phenylalanine methyl ester, alanine methyl ester, or a side chain-protected arginine methyl ester). The resin beads bearing the coupled products are combined, mixed and redivided into portions, and the hydroxy group of each portion reacted with the carboxyl group of a series of N-protected (for example protected by 9-fluorenylmethoxycarbonyl "Fmoc" amino acids (for example valine, tyrosine, alanine, glycine, piperidine-4-carboxylic acid, 3-(aminomethyl)benzoic acid) to form an ester (the X bridging group). The resin beads bearing the ester linkage thus formed are combined, mixed and redivided into portions. The amino groups are deprotected and linked with a series of amino acids to which a dye has been appended (dye-tyrosine, dye-glycine, dye-aspartate, and the like). The resin beads bearing the product are then sequentially combined, mixed, redivided and reacted in the same manner with further N-protected amino acids (leucine, serine, lysine, D-alanine, proline, O-benzylserine, 3-(aminomethyl)benzoic acid), followed by a further series of N-protected amino acids (serine, threonine, threonine, allo-threonine, D-serine, glutamine, lysine, glycine, 1-aminocyclopentanecarboxylic acid, valine, histidine, homoserine, isoserine, β-alanine, aspartic acid, alanine). As a final step, the N-protecting groups of the last series of amino acids are removed to form an acyclic compound of Formula I.

In this example, the library of 19,875 different compounds that has been assembled on resin is screened by the method described above for cyclization in the presence of a peptidase.

The steps of the invention are described in more detail.

Step 1—Formation of the Compound of Formula I

The formation of the compounds of Formula I is by any conventional means; such syntheses are well known in the art. For example, the synthesis of polypeptides by utilizing solid phase techniques on resins is exhaustively discussed in the literature. See, for example, Solid Phase Synthesis—Peptides, Polypeptides and Olignucleotides, Editor Roger Epton, Published by SPCC UK Ltd., the disclosure of which is hereby incorporated by reference. An example of such syntheses is given in the following Examples.

One subunit of those comprising $R^1$ and $R^2$ is chosen to be linked to a resin via a "linker". Examples of such resins are crosslinked polystyrene beads, PEGA (polyethyleneglycol-polyacrylamide) beads, and the like. The linkage to the resin can be through an amide bond, an ether bond, or other linkages that are stable to the conditions for cleavage of the group X. For example, the resin may be linked to $R^1$ or $R^2$ via a dicarboxylic acid, preferably a succinyl or glutaryl group, through attachment of a carboxyl group on $R^1$ or $R^2$ directly to an amino group on the resin (to form an amide), or through attachment of an oxygen, sulfur or nitrogen group on $R^1$ or $R^2$ to a group on the resin to form an ether, sulfide or amine linkage respectively.

One subunit of those comprising $R^1$ and $R^2$ is chosen to be linked to a dye molecule. Examples of such dye molecules are 2-(N-(4-(4-nitrophenylazo)phenyl)-N-ethylamino)ethyl (Disperse Red 1) and analogs thereof, and such dyes as xylenol orange, malachite green, Coomassie blue, and the like. They are attached to $R^1$ and $R^2$ by an amide bond, an ether bond, or any other bond that is stable to the conditions required for the cleavage of X.

X can be any bridging moiety that is cleavable under reaction conditions that do not cleave an amide formed by cyclization of the precursor of formula (1), or cleave the linkage of $R^1$ and $R^2$ to the resin or the dye molecule. Such bridging moieties include an ester linkage (cleaved by treatment with a base), a disulfide linkage (cleaved by reduction), a —CH(OH)—CH(OH)— linkage (cleaved by oxidation), a carbonate linkage (cleaved by base), and the like. The group X may be introduced in the process of joining two subunits of $R^1$ and/or $R^2$ together, or by incorporating a subunit that already contains such a group X in the assembly of the precursor of formula (1). For example, an ester group can be introduced as the bridging group X by coupling a carboxyl group on one subunit with a hydroxyl group on a second subunit by means well known in the art. One example would be coupling the carboxylic acid of an amino acid subunit with a hydroxy group of threonine, serine, or hydroxyproline. A carbonate group can be introduced as the bridging group X by linking two hydroxyl-containing subunits together be means of p-nitrophenyl chloroformate, phosgene, or phosgene-related reagents. A disulfide linkage can be introduced as the bridging group X by incorporating subunits that contain this function, for example the amino acid $NH_2CH_2CH_2$—S—S—$CH_2CO_2H$, and a —CH(OH)—CH(OH)— linkage can be introduced as the bridging group X by incorporating subunits that contain a tartaric acid moiety.

In addition to the acylation reactions of peptide synthesis that allow amino acid subunits to be assembled, whether by solid phase reactions or by conventional syntheses, any other reactions that are useful in organic synthesis for forming bonds can be employed in joining together appropriate subunits of the acyclic precursor of formula (1), provided that they are compatible with solid-supported synthesis methods and with other functionalities in the molecules, for example the X group, the linkage to the resin and the dye molecule, and the like. Such reactions that are compatible with solid phase are described in Synthesis and Applications of Small Molecule Libraries, by Thompson et al., *Chem. Rev.* (1996), Vol. 96, pp 555–600; The Design of Compound Libraries and Their Application to Drug Discovery, *Tetrahedron* (1995), Vol. 51, pp 8135–8173; Combinatorial Chemistry, *Chem. Soc. Rev.*, (1995), pp 309–317.

Step 2—Cyclization Reaction

The product of step 1 is then contacted with a peptidase under conditions that allow formation of a peptide bond between an amino group and a group -COY as defined above. Examples of suitable peptidases include, but are not limited to, serine peptidase such as trypsin, thrombin, and elestase, CMV protease, aspartic peptidases such as pepsin, renin, HIV protease, and cathepsin D, zinc peptidases such as matrilysin, stromelysin, angiotensin converting enzyme, and cysteine peptidases such as cathepsins B, K and L, and the caspases, and HCV protease. The product is separated by filtration.

Step 3—Cleavage of X

The product from step 2 is then treated under reaction conditions suitable for cleaving X without cleaving the amide bond(s). For example, if X is an ester or a carbonate, treatment with solution of an alkoxide or hydroxide ions, for example methanolic or aqueous sodium hydroxide, at about room temperature for 2–12 hours selectively cleaves the ester or carbonate bond. Similarly, if X is a disulfide bond, it can be cleaved by reduction, for example with dithiothreitol or dithioerythritol. If X is a —CH(OH)—CH(OH)— moiety, it can be cleaved by oxidation, for example with sodium periodate. The product of step 3 is then filtered off and washed with an inert solvent, for example methanol/water, to give a resinous product.

Retention of the dye on the resin beads product of step 3 indicates that cyclization has taken place; a colorless resin and observation of the dye in the filtrate indicates that cyclization has not taken place. The specific analogs that afford positive results in this screen may be then identified by conventional analysis of the material that is isolated from the resin beads by cleaving the bond linking the material to the resin beads. See, for example, "A Mass Spectometric Solution to the Address Problem of Combinatorial Libraries", *Science* (1994), Vol. 264, 399–402, or by reading the coding on a specific bead, if the synthesis was carried out using an encoding method; (see, for example, "Complex Synthetic Chemical Libraries Indexed with Molecular Tags" by Ohlmeyer et al., *Proc. Nat. Acad. Sci.* USA, (1993), Vol. 90, pp 10922–10926), or through deconvolution by resynthesis (se, for example, "Recursive deconvolution of Combinatorial Chemical Libraries", by Erb et al., *Proc. Nat. Acad. Sci.* USA, (1994), Vol. 91, pp 11422–11426).

The validity of this approach was confirmed as follows. Acyclic compounds of Formula III was assembled conventionally:

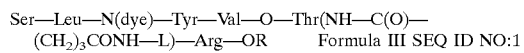

Formula III SEQ ID NO:1 where L is hydrogen or a resin plus linker and R is hydrogen or methyl.

The compound of Formula III SEQ ID NO: 1 where R is methyl and L is hydrogen was readily cyclized by trypsin in 30:30:40 DMF/ethanol/pH 6.5 Tris buffer to give compound A, affording also some hydrolyzed product B (i.e. where R is hydrogen). The structure was determined conventionally.

The compound of Formula III SEQ ID NO: 1 where L is a resin linker was treated in the same manner, and the resin component removed. The same products A and B were obtained as when L is hydrogen. Therefore the material on the resin is accessible to the enzyme. A control experiment without the enzyme gave only starting material.

The compound of Formula III SEQ ID NO: 1 where L is a resin linker was treated by trypsin in 30:30:40 DMF/ethanol/pH 6.5 Tris buffer, and then cleaved with 1:1 methanol/IM sodium hydroxide, filtered and washed. The color was retained on the resin.

The compound of Formula III SEQ ID NO: 1 where L is a resin linker was treated with 1:1 methanol/IIM sodium hydroxide, filtered and washed. The beads were colorless (i.e. the color was not retained on the resin), but the color was seen in the filtrate.

The following Examples illustrate one aspect of the invention but are not intended to limit its scope.

In contrast to the foregoing, the following Examples indicate that a "photolinker" has been inserted between the resin and the glutaryl sidechain. This was inserted in order to provide convenient and easy detachment of the molecules from the resin so that structures of the products could be determined. The invention would be operable in the presence or absence of such a photolinker, but the photolinker is clearly not necessary for the application of the invention.

EXAMPLES

General

Reagents and solvents were obtained from commercial suppliers and used as received. Trypsin (from bovine pancrease, Type I, ethanol precipitate) and N-α-benzoyl-L-arginine-p-nitroanilide, hydrochloride were obtained from Sigma®. All moisture- or air-sensitive reactions were conducted under nitrogen in dried solvents. Unless otherwise indicated, chromatography was performed on silica gel with the indicated solvent as eluant. Preparative reverse phase HPLC was performed on a Vydaio® (Fluorocarbon+clomer) C18 peptide and protein column under the following conditions: solvent A=H.$_2$(w/0.01% TFA), solvent B=$CH_3CN$ (0.01% TFA); flow rate=10 ml/min; time table: 0 min—95% A/5% B, 42 min—30% A/70% B, 50 min—5% A/95% B, 54 min—95% A/5% B, 56 min—95% A/5% B. Analytic reverse phase HPLC was performed on a Rainan® microsorb C18, 100 A°, 5 mm, 25 cm, 4 mm id column under the following conditions: solvent A=$H_2O$ (w/0.01% TFA), solvent B=$CH_3CN$ (0.01% TFA); flow rate=2 ml/min; time table: 0 min—95% A/5% B, 5 min—40% A/60% B, 10 min—15% A/85% B, 12 min—5% A/95% B, 14 min—95% A/5% B, 16 min—95% A/5% B. Spectral data are reported as chemical shifts (multiplicity, coupling constants in Hz, number of hydrogens). A number preceding multiplicity refers to peaks due to conformational isomerization. $^1$H NMR spectral data are referenced to $CHCl_3$ (7.26 ppm) or $CHD_2OD$ (3.30 ppm); $^{13}$C NMR were proton decoupled and chemical shifts are referenced to $CDCl_3$ (77.0 ppm) or $CD_3OD$ (49.0 ppm). Mass spectra were obtained by the Mass Spectrometry Laboratory of the College of Chemistry, University of California, Berkeley. Abbreviations used: HOBT, 1-hydroxybenzotriaxole; EDC, 1-(3-(dimethylamino)propyl)-3-ethylcarbodiimide; TFA, trifluoracetic acid; TRIS, tris(hydroxymethyl)aminomethane; L-BAPNA, N-α-benzoyl-L-arginine-p-nitroanilide, hydrochloride; DIEA, diisopropylethylamine; DMF, dimethylformamide; DMAP, 4-(dimethylamino)pyridine.

SEQUENCE FOR ASSEMBLY OF ACYCLIC PRECURSOR OF FORMULA I AND CYCLIZATION WITH TRYPSIN

EXAMPLE 1

Synthesis of Acyclic Resin Bound Enzymatic Substrates and Acyclic Depsipeptide (1) Glutaric Acid, Trimethylsilylethyl Ester A solution of 1.30 g of trimethylsilylethanol (11.0 mmol, 1.1 eq), 1.14 g of glutaric anhydride (10 mmol, 1.0 eq), 1.53 mL of $Et_3N$ (11 mmol, 1.1 eq) and 122 mg of DMAP (1 mmol, 0.1 eq) in 50 mL of $CH_2Cl_2$ was stirred under $N_2$ for 18 h. The solution was partitioned between $CH_2Cl_2$ (250 mL) and 1M HCl (600 mL) and the organic layer was dried and evaporated to give 2.34 g of the glutaric acid monoester (100%).

$^1$H NMR (300 MHz, $CDCl_3$) δ4.18 (m, 2H), 2.41 (t, J=7.2 Hz, 2H), 2.38 (t, J=7.2 Hz, 2H), 1.9 (quintet, J=7.2 Hz, 2H), 0.97 (m, 2H), 0.04 (s, 9H).

(2) N-[Glutaryl(trimethylsilylethyl ester)]-L-threonine

To a solution of 10 g of N-Boc-L-threonine (45.6 mmol, 1.0 eq), 4.93 g of benzyl alcohol (45.6 mmol, 1.0 eq) and 556 mg of DMAP (4.5 g mmol, 0.1 eq) in 85 mL $CH_2Cl_2$ at $-5°$ C. under $N_2$ was added 9.62 g of EDC (50.1 mmol, 1.1 eq). The resultant solution was allowed to warm to room temperature with stirring over 18 h. After removal of solvents in vacuo, the residue was partitioned between EtOAc (1 L) and $H_2O$ (200 mL). The organic layer was washed with $H_2O$ (1×200 mL), $NaHCO_3$(sat) (2×600 mL) and then $H_2O$ again (3×500 mL), dried and evaporated yielding 14.1 g (100%) of the benzyl ester (Rf=0.24, in 25% EtOAc/Hex). To 14.1 g of the benzyl ester (45.6 mmol, 1.0 eq) was added 120 mL of 4M HCl in dioxane (480 mmol, 10.5 eq) and the solution was stirred for 3.5 h. Upon concentrating, 10.76 g (97%) of the amine hydrochloride was obtained.

To a solution of 10.76 g of the amine hydrochloride (43.9 mmol, 1.0 eq), 10.19 g of glutaric mono TMS-ethyl ester mono acid (43.0 mmol, 1.0 eq)), 5.92 g of HOBT (43.9 mmol, 1.0 eq), and 6.09 mL of Et3N (43.9 mmol, 1.0 eq) in DMF (80 mL) at $-5°$ C. was added 8.39 g of EDC (43.9 mmol, 1.0 eq). The solution was allowed to warm to room temperature over 22 h, at which time removal of the DMF and column chromatography yielded 10.74 g (58%) of the threonine-glutaric ester adduct, (Rf=0.45 in 15% acetone/$CH_2Cl_2$).

To 8.24 g (19.48 mmol, 1.0 eq) of the benzylester-Thr-glutaric ester in 80 mL MeOH was added 4.09 g of 10% Pd/C (3.90 mmol, 0.2 eq). Air was removed via a $H_2O$ aspirator and the reaction was put under and H2 atmosphere via a balloon. After 4 h, the reaction was filtered through a pad of Celite (5cm×1.5 inch) yielding, after removal of solvent, 5.72 g (88%) of the acid.

$^1$H NMR (300 MHz, $CDCl_3$) δ5.67 (bs, 1H), 4.49 (m, 2H), 4.17 (t, J=8.6 Hz, 2H), 2.38 (m, 3H), 1.99 (m, 2H), 1.24 (d, J=6.3 Hz, 3H), 0.99 (t, J=8.6 Hz 2H), 0.04 (s, 9H).

(3) N8-[4-methoxy-2,3,6-trimethyl benzenesulfonyl]-L-arginine, Methyl Ester

To a solution of 3.86 g of $N_2$-carbobenzyloxy-N8-[4-methoxy-2,3,6-trimethyl benzenesulfonyl]-L-arginine (7.42 mmol, 1.0 eq), 3.0 mL of MeOH (74.23 mmol, 10.0 eq) and 90 mg of DMAP (0.74 mmol, 0.1 eq) in 20 mL of $CH_2Cl_2$ at 0° C. was added 1.56 g of EDC (8.17 mmol, 1.1 eq). The solution was stirred as it warmed to room temperature over 18 h. After concentrating the solution, the residue was partitioned between EtOAc (225 mL) and $H_2O$ (40 mL); the organic layer was washed with $NaHCO_3$(sat.) (2×40 mL) and $H_2O$ (2×40 mL), dried and evaporated yielding 3.78 g of the Me ester, (Rf=0.64, 30% acetone/$CH_2Cl_2$).

A solution of 3.78 g of the arginine methyl ester (7.08 mmol, 1.0 eq) in 19 mL MeOH was hydrogenated with 1.45 g 10% Pd/C (1.4 mmol, 0.2 eq) under an H2 balloon for 4 h, which after filtering through a pad of Celite and removal of solvent yielded 2.59 g of N8-[4-methoxy-2,3,6-trimethyl benzenesulfonyl]-L-arginine, methyl ester (91%) as a white solid.

$^1$H NMR (300 MHz, CDCl$_3$) δ6.52 (s, 1H), 6.32 (bs, 1H), 6.22 (bs, 2H), 3.82 (s, 3H), 3.70 (s, 3H), 3.46 (m, 1H), 3.16 (m, 2H), 2.68 (s, 3H), 2.60 (s, 3H), 2.12 (s, 3H), 1.74 (m, 1H), 1.60 (m, 4H)

(4) N-[Glutaryl(trimethylsilylethyl ester)]-L-threonyl - N8[4-methoxy-2,3,6-trimethyl benzenesulfonyl]-L-arginine, Methyl Ester To a solution of 1.88 g of N8-[4-methoxy-2,3,6-trimethyl benzenesulfonyl]-L-arginine, methyl ester. (4.70 mmol, 1.0 eq), 1.72 g of N-[glutaryl(trimethylsilylethyl ester)]-L-threonine (5.16 mmol, 1.1 eq), 634 mg of HOBT (4.70 mmol, 1.0 eq) and 0.9 mL of DIEA (5.16 mmol, 1.1 eq) in 40 mL DMF at –5° C. was added 987 mg of EDC (5.16 mmol, 1.1 eq). The solution was allowed to warm to room temperature as it stirred in the bath for 14 h. Upon removal of the DMF in vacuo the residue was partitioned between CH$_2$Cl$_2$ (100 mL) and H$_2$O (850 mL). The aqueous layer was extracted with CH$_2$Cl$_2$ (14×100 mL). The combined organic layer was then washed with 1M HCl (2×300 mL), NaHCO$_3$(sat.) (2×300 mL), and NaCl(sat.) (300 mL) dried and evaporated yielding, after column chromatography, 2.69 g (80%) of the amide.

$^1$H NMR (300 MHz, CDCl$_3$) δ7.57 (d, J=7.5 Hz, 1H), 7.02 (d, J=7.8 Hz, 1H), 6.52 (s, 1H), 6.35 (bs, 2H), 6.17 (bs, 1H), 4.46 (m, 2H), 4.30 (bs, 1H), 4.13 (m, 2H), 3.82 (s, 3H), 3.71 (s, 3H), 3.16 (m, 2H), 2.66 (s, 3H), 2.59 (s, 3H), 2.28 (m, 4H), 2.11 (s, 3H), 1.90 (m, 3H), 1.75 (m, 1H), 1.41 (m, 2H), 1.15 (d, J=6.4 Hz, 3H), 0.96 (m, 2H), 0.02 (s, 9H); $^{13}$C NMR (100 MHz, CDCl$_3$) δ173.5, 173.1, 172.1, 171.1, 158.3, 156.2, 138.2, 136.2, 133.2, 124.6, 111.5, 67.2, 62.5, 57.9, 55.2, 52.2, 52.1, 40.4, 34.9, 33.2, 28.5, 25.0, 23.9, 20.7, 18.7, 18.1, 17.1, 11.7, –1.7; HRMS(FAB) Calcd for C$_3{}^1$H$_{54}$N$_5$O$_{10}$SiS(MH+): 716.3367, found 716.3360; Rf: 0.53 in 10% acetone/CH$_2$Cl$_2$

(5) O-[N-(carbobenzyloxy)valinyl]-N-[glutaryl (trimethylsilylethyl ester)]-L-threonyl-N8[4-methoxy-2,3,6-trimethyl benzenesulfonyl]-L-arginine, Methyl Ester To a solution of 8.36 g of N-α-carbobenzyloxy-L-valine (33.3 mmol, 1.0 eq), 7.94 g of N-[glutaryl (trimethylsilylethyl ester)]-L-threonyl - N8[4-methoxy-2,3,6-trimethyl benzenesulfonyl]-L-arginine, methyl ester (11.10 mmol, 1.0 eq) and 135 mg of DMAP (1.10 mmol, 0.1 eq) in 40 mL CH$_2$Cl$_2$ at –5° C. was added 6.36 g EDC (33.3 mmol, 3.0 eq). After stirring for 19 h as the solution warmed to room temperature, the solvent was removed in vacuo. The residue was partitioned between EtOAc (1.1 L) and H$_2$O (250 mL). The organic layer was then washed with NaHCO$_3$ (sat.) (2×400 mL), H$_2$O (2×400 mL), dried, evaporated and purified by column chromatography, yielding 8.87 g of the ester product, (84%).:

$^1$H NMR (300 MHz, CDCl$_3$) δ7.32 (m, 5H), 6.85 (bs, 1H), 6.51 (s, 1H), 6.16 (bs, 2H), 5.99 (bs, 1H), 5.67 (bs, 1H), 5.47 (bs, 1H), 5.05 (m, 2H), 4.69 (m, 1H), 4.53 (m, 1H), 4.12 (m, 3H), 3.81 (s, 3H), 3.71 (s, 3H), 3.15 (m, 2H), 2.68 (s, 3H), 2.63 (s, 3H), 2.27 (m, 4H), 2.12 (s, 3H), 1.94–1.89 (m, 3H), 1.71 (m, 2H), 1.48 (m, 1H), 1.27 (d, J=6.6 Hz, 3H), 0.99–0.90 (m, 8H), 0.02 (s, 9H); Rf: 0.56, 30% acetone/CH$_2$Cl$_2$

(6) N-[(4-nitrophenylazo)-2-aminophenylethyl-N-ethyl], O-tert-butyl-L-tyrosine To a solution of 4.73 mL of oxalyl chloride (54.6 mmol, 2.7 eq) in 25 mL of CH$_2$Cl$_2$ at –78° C. was added 5.68 ml of DMSO (80 mmol, 4.0 eq) in 25 mL of CH$_2$Cl$_2$ dropwise. After stirring for 15 min at –78° C., 6.24 g of Disperse Red 1 (20 mmol, 1.0 eq) in 50 mL of 1:1 DMSO/CH$_2$Cl$_2$ was added dropwise. After stirring the reaction at –78° C. for 1 h, 19.4 mL of Et3N (140 mmol, 7.0 eq) was added. The bath was then removed and the mixture was allowed to warm to room temperature. The reaction was partitioned between CH$_2$Cl$_2$ (400 mL) and H$_2$O (400 mL). The aqueous layer was extracted further with CH$_2$Cl$_2$ (2×300 mL) and the combined organic layer was dried, evaporated and chromatographed (1% acetone/CH$_2$Cl$_2$) yielding 5.72 g of the aldehyde, (92%). Rf: 0.58, 1% acetone/CH$_2$Cl$_2$.

To a solution of 1.91 g of the aldehyde (6.13 mmol, 1.0 eq) and 2.0 g of O-(tert-butyl)-L-tyrosine, methyl ester in 195 mL dichloroethane was added 1.82 g of NaBH(OAc)3 (8.58 mmol, 1.4 eq). After stirring under N$_2$ for 1.5 h, the solution was concentrated to ca. 80 mL and applied directly to a 9 cm×6 inch SiO$_2$ column. After elution with 1% (3 L) to 2.5% (2 L) to 10% (2 L) acetone/CH$_2$Cl$_2$ and concentration, 1.34 g of the monoalkylated tyrosine methyl ester was obtained, (40%). Rf: 0.20, 1% acetone/CH$_2$Cl$_2$.

To 3.63 g of the above ester (6.64 mmol, 1.0 eq) in 110 mL of 2:1 THF/MeOH was added 10 mL 1.0M LiOH (9.95 mmol, 1.5 eq). After stirring for 8 h, CH$_2$Cl$_2$ (1L) and NaCl(sat.)(500 mL) were added. The aqueous layer was extracted further with CH$_2$Cl$_2$ (2×200 mL). The combined organic layer was dried and evaporated, yielding 3.2 g of the acid, (91%).

$^1$H NMR (300 MHz, CD$_3$OD) 8.34 (d, J=9.1 Hz, 2H), 7.93 (d, J=9.1 Hz, 2H), 7.84 (d, J=9.2 Hz, 2H), 7.16 (d, J=8.4 Hz, 2H), 6.85 (d, J=8.4 Hz, 2H), 6.82 (d, J=9.4 Hz, 2H), 3.55–3.45 (m, 4H), 2.95–2.67 (m, 5H), 1.28 (s, 9H), 1.16 (t, J=6.8 Hz, 3H); $^{13}$C NMR (100 MHz, CD$_3$OD) δ181.2, 158.2, 154.8, 153.2, 148.5, 144.7, 135.4, 130.9, 127.4, 125.6, 125.0, 123.5, 112.6, 79.3, 67.1, 50.9, 46.6, 46.3, 40.5, 29.2, 12.6; HRMS(FAB) Calcd for C$_{29}$H$_{36}$N$_5$O$_5$ (MH+): 534.2726, found 534.2716; Rf: 0.23, 10% MeOH/CH$_2$Cl$_2$

(7) O-{[(4-nitrophenylazo)-2-aminophenylethyl-N-ethyl]-O-tert-butyl-L-tyrosinyl-L-valinyl]}-N-[glutaryl(trimethylsilylethyl ester)]-L-threonyl - N8 [4-methoxy-2,3,6-trinethylbenzenesulfonyl]-L-arginine, Methyl Ester A mixture of 4.05 g of O-[N-(carbobenzyloxy)valinyl]-N-[glutaryl(trimethylsilylethyl ester)]-L-threonyl—N8[4-methoxy-2,3,6-trimethyl benzenesulfonyl]-L-arginine, methyl ester (4.27 mmol, 1.0 eq) and 1.79 g of 5% Pd/C (0.85 mmol, 0.2 eq) in 30 mL MeOH was placed under a H2 balloon and stirred for 2 h. Upon filtering through a small pad of Celite and removal of the solvent, 3.30 g of the corresponding free amine was obtained.

To a solution of 3.19 g of N-[(4-nitrophenylazo)-2-aminophenylethyl-N-ethyl], 0-tert-butyl -L-tyrosine (5.98 mmol, 1.4 eq), 3.47 g of the aforementioned amine (4.27 mmol, 1.0 eq), 830 mg of HOBT (6.15 mmol, 1.44 eq) and 2.13 mL of DIEA (12.30 nmmol, 2.88 eq) in DMF (110 mL) at –5° C. was added 1.17 g of EDC (6.15 mmol, 1.44 eq). The mixture was stirred for 17 h as it warmed to room temperature, at which time the DMF was removed in vacuo. The residue was partitioned between CH$_2$Cl$_2$ (150 mL) and H$_2$O (800 mL), and the aqueous layer was extracted further with CH$_2$Cl$_2$ (3×150 mL). The combined organic layer was washed with 1M HCl (2×150 mL), NaHCO$_3$(sat.) (2×150 mL), NaCl(sat.) (1×150 mL), dried, evaporated and purified by chromatography yielding 3.86 g of the amide, (68%).

$^1$H NMR (300 MHz, CDCl$_3$) δ8.32 (d, J=8.9 Hz, 2H), 7.91 (d, J=8.9 Hz, 2H), 7.86 (d, J=9.0 Hz, 2H), 7.45 (d, J=7.9

Hz, 1H), 6.96 (d, J=8.3 Hz, 2H), 6.85 (d, J=8.3 Hz, 2H), 6.72 (d, J=9.2 Hz, 2H), 6.51 (s, 1H), 6.39 (bs, 2H), 6.17 (bs, 1H), 5.52 (m, 1H), 4.76 (m, 1H), 4.56 (m, 1H), 4.31 (m, 1H), 4.14 (m, 2H), 3.80 (s, 3H), 3.77 (m 1), 3.70 (s, 3H), 3.50–3.03 (m, 8H), 2.79 (bs, 2H), 2.69 (s, 3H), 2.63 (s, 3H), 2.25 (m, 4H), 2.11 (s, 3H), 1.92–1.30 (m, 9H), 1.30 (s, 9H), 1.28 (d, J=7.2 Hz, 3H), 1.10 (t, J=6.9 Hz, 3H), 0.96 (m, 2H), 0.89 (d, J=6.8 Hz, 3H), 0.83 (d, J=6.8 Hz, 3H), 0.03 (s, 9H); HRMS(FAB) Calcd for $C_{65}H_{96}N_{11}O_{15}SSi(MH+)$: 1330.6557, found 1330.6577; Rf: 0.72, 30% acetone/$CH_2Cl_2$ (8) O-{N-[(9-fluorenylmethoxycarbonyl)-L-leucyl]-N-[(4-nitrophenylazo)-2-aminophenylethyl-N-ethyl]—O-tert-butyl -L-tyrosinyl-L-valinyl}-N-[glutaryl(trimethylsilylethyl ester)]-L-threonyl-N8 [4-methoxy-2,3,6-trimethylbenzenesulfonyl]-L-arginine, Methyl Ester A solution of 0.84 g of O-{[(4-nitrophenylazo)-2-aminophenylethyl-N-ethyl]—O-tert-butyl-L-tyrosinyl-L-valinyl]}-N-[glutaryl(trimethylsilylethyl ester)]-L-threonyl-N8[4-methoxy-2,3,6-trimethyl benzenesulfonyl]-L-arginine, methyl ester (0.63 mmol, 1.0 eq), 5.63 g of FmocNHLeu acid fluoride (15.8 mmol, 25.0 eq) and 3.24 g of 2,6 di-t-Bu-4-methyl pyridine (15.8 mmol, 25.0 eq) in 4 mL DMF was stirred under $N_2$ for 120 h. After removal of the DMF in vacuo, $CH_2Cl_2$ (20 mL) and $H_2O$ (600 mL) were added. Further extraction of the aqueous layer with $CH_2Cl_2$ (4×20 mL), followed by washing of the combined organics with 1M HCl (2×250 mL), $NaHCO_3$(sat.) (2×250 ml), NaCl(sat.) (1×250 mL) yielded after drying over MgSO4, $SiO_2$ column chromatography, and size exclusion chromatography with Sephadex (LH-20), 545 mg amide product (52%) and 90 mg of recovered starting material amine.

$^1$H NMR (300 MHz, CDCl$_3$) δ8.34–8.31 (m, 2H), 8.11 (d, J=6.0 Hz, 1H), 7.93–7.87 (m, 4H), 7.77–7.72 (m, 2H), 7.58–7.26 (m, 6H), 7.07–6.85 (m, 6H), 6.77–6.70 (m, 2H), 6.48 (s, 1H), 6.36 (bs, 1H), 6.24 (bs, 1H), 5.92 (bs, 1H), 5.67 (bs, 1H), 4.71 (m, 1H), 4.56–4.43 (m, 3H), 4.27–4.06 (m, 4H), 3.78 (2s, 3H), 3.70 (2s, 3H), 3.45–3.06 (m, 7H), 2.67 (2s, 3H), 2.60 (2s, 3H), 2.36–2.29 (m, 4H), 2.09 (s, 3H), 1.95–1.53 (m, 9H), 1.33–1.11 (m, 15H), 0.98–0.73 (m, 14H), 0.00 (2s, 9H); HRMS(FAB) Calcd for $C_{86}H_{117}N_{12}O_{18}SiS(MH+)$: 1665.8112, found 1665.8099; Rf: 0.74, 30% acetone/$CH_2Cl_2$ (9) O-{N-[(N-tert-butoxycarbonyl, O-tert-butyl)-L-serinyl-L-leucyl]-N-[(4-nitrophenylazo)-2-aminophenylethyl-N-ethyl], O-tert-butyl -L-tyrosinyl-L-valinyl}-N-[glutaryl(trimethylsilylethyl ester)]-L-threonyl—N8[4-methoxy-2,3,6-trimethylbenzenesulfonyl]-L-arginine, Methyl Ester A solution of 545 mg of O-{N-[(9-fluorenylmethoxycarbonyl)-L-leucyl]-N-[(4-nitrophenylazo)-2-aminophenylethyl-N-ethyl]—O-tert-butyl-L-tyrosinyl-L-valinyl}-N-[glutaryl(trimethylsilylethyl ester)]—N8[4-methoxy-2,3,6-trimethylbenzenesulfonyl]-L-arginine, methyl ester (0.33 mmol, 1.0 eq) and 0.33 mL of piperidine (3.3 mmol, 10.0 eq) in 6 mL $CH_2Cl_2$ were stirred for 2 h. Upon removal of solvent and purification by size exclusion chromatography, Sephadex (LH-20), 471 mg of the amine product was obtained, (99%).

To a solution of 2.38 g of the resultant amine (1.65 mmol, 1.0 eq), 1.29 g N-Boc-Ser(O-t-Bu)CO2H (4.95 mmol, 3.0 eq), 669 mg of HOBT (4.95 mmol, 3.0 eq) and 0.86 mL of DIEA (4.95 mmol, 3.0 eq) in 25 mL DMF at −5° C. was added 946 mg EDC (4.95 mmol, 3.0 eq). After warming up to room temperature over 10 h, the DMF was removed in vacou. The residue was partioned between $CH_2Cl_2$ (100 mL) and $H_2O$ (800 mL). Further extraction of the aqueous layer with $CH_2Cl_2$ (3×100 mL), followed by washing of the combined organics with 1M HCl (2×150 mL), $NaHCO_3$ (sat.) (2×150 ml), and NaCl(sat.) (1×150 mL) yielded after drying, evaporation and chromatography, 2.38 g of the amide product, (86%).

$^1$H NMR (300 MHz, CD$_3$OD) δ8.20 (d, J=9.3 Hz, 2H), 7.90 (m, 4H), 7.18–7.11 (m, 2H), 7.02 (d, J=9.0 Hz, 2H), 6.92 (d, J=8.4 Hz, 2H), 6.86 (d, J=9.0 Hz 1H), 6.62 (s, 1H), 6.49 (bs, 1H), 5.27 (m, 2H), 4.71 (m, 1H), 4.67 (d, J=5.4 Hz, 1H), 4.43 (m, 1H), 4.27 (m, 2H), 4.10 (m, 2H), 3.80 (s, 3H), 3.71–3.39 (m, 12H), 3.17–3.14 (m, 4H), 2.64 (s, 3H), 2.58 (s, 3H), 2.38–2.30 (m, 5H), 2.08 (s, 3H), 1.93–1.56 (m,9H), 1.55–1.14 (m, 33H), 1.05–0.76 (m, 14H), 0.01 (s, 9H); HRMS(FAB) Calcd for $C_{83}H_{128}N_{13}O_{20}SiS(MH+)$: 1686.8911, found 1686.8889; Rf: 0.79, 30% acetone/$CH_2Cl_2$

(10) O-{N-[(N-tert-butoxycarbonyl, O-tert-butyl)-L-serinyl-L-leucyl]-N-[(4-nitrophenylazo)-2-amninophenylethyl-N-ethyll, O-tert-butyl -L-tyrosinyl-L-valinyl}-N-(glutaric acid)-L-threonyl—N8[4-methoxy-2,3,6-trimethyl benzenesulfonyl]-L-arginine, Methyl Ester To a solution of 508 mg of O-{N-[(N-tert-butoxycarbonyl, O-tert-butyl)-L-serinyl-L-leucyl]-N-[(4-nitrophenylazo)-2-aminophenylethyl-N-ethyl], O-tert-butyl-L-tyrosinyl-L-valinyl}-N-[glutaryl(trimethylsilylethyl ester)]-L-threonyl—N8 [4-methoxy-2,3,6-trimethyl benzenesulfonyl]-L-arginine, methyl ester (0.30 mmol, 1.0 eq) in 4 mL DMF was added 0.75 mL of 1.0 M TBAF in THF (0.75 nunol, 2.5 eq). After stirring for 6 h, the solution was partitioned between EtOAc (250 mL) and $H_2O$ (250 mL). The organic layer was washed with NaCl(sat.) (250 mL), dried, evaporated and purified by size exclusion chromatography, Sephadex (LH-20), yielding 288 mg of the acid product, (60%).:

$^1$H NMR (300 MHz, CD$_3$OD) δ8.56 (bs, 1H), 8.24 (m, 2H), 7.85 (m, 4H), 7.18–7.09 (m, 2H), 7.01–6.85 (m, 4H), 6.58 (s, 1H), 6.42 (bs, 1H), 5.30–5.21 (m, 2H), 4.79–4.67 (m, 2H), 4.44–4.20 (m, 3H), 3.77 (s, 3H), 3.67 (s, 3H), 3.64–3.34 (m, 6H), 3.25–3.17 (m, 4H), 2.63 (s, 3H), 2.56 (s, 3H), 2.37–2.14 (m, 4H), 2.05 (s, 3H), 1.93–1.57 (m, 9H), 1.44–1.13 (m, 33H), 1.04–0.75 (m, 12H); HRMS (FAB) Calcd for $C_{78}H_{116}N_{13}O_{20}S(MH+)$: 1586.8175, found 1586.8180; Rf: 0.35, 10% MeOH/$CH_2Cl_2$.

(11) 4-[4-{1-(9-Fluorenylmethoxycarbonylamino)ethyl}-2-methoxy-5-nitrophenoxy]butan-PEGA-amide and 4-[4-{1-(9-Fluorenylmethoxycarbonylamino)ethyl}-2-methoxy-5-nitrophenoxy]butan-Tentagel-amide Prepared as described in Holmes, C. P.; Jones, D. G. *J. Org. Chem.* 1995, 60, 2318–2319.

(12) O-{N-[L-Serinyl-L-leucyl]-N-[(4-nitrophenylazo)-2-aminophenylethyl-N-ethyl]-L-tyrosinyl-L-valinyl}-N-(glutaryl-photolinker-Tentagel-amide)-L-threonyl-L-arginine, Methyl Ester A slurry of 485 mg of 4-[4-{1-(9-fluorenylmethoxycarbonylamino)ethyl}-2-methoxy-5-nitrophenoxy]butan-Tentagel-amide in 5 mL of 20% piperidine/DMF was agitated for 1 min, filtered and upon addition of 5 mL more of 20% piperidine/DMF agitated for 1 h. Upon filtering, the resin was washed with DMF (5 mL×5 min×5). The deprotected amino resin was then treated with a solution of 355 mg of O-{N-[(N-tert-butoxycarbonyl, O-tert-butyl)-L-serinyl-L-leucyl]-N-[(4-nitrophenylazo)-2-aminophenylethyl-N-ethyl], 0-tert-butyl -L-tyrosinyl-L-valinyl}-N-(glutaric acid)-L-threonyl - N8[4-methoxy-2,3,6-trimethyl benzenesulfonyl]-L-arginine, methyl ester (0.22 mmol, 1.54 eq) and 36 mg of HOBT (0.27 mmol, 1.86 eq) in 5 mL of DMF. After agitating for 10 min, 39 mL of diisopropylcarbodiimide (0.25 mmol, 1.71 eq) was added. After agitating for 19 h, the slurry was filtered, and the resin was washed with DMF (5 mL×5 min×6), $CH_2Cl_2$ (5 mL×5 min×6), and dried in vacuo. The resin (3b) was treated with an 85% TFA/5% phenol/5% thiophenol/5% thioanisole (% by weight) cleavage cocktail (4 mL×1 min, than 6 mL×28 h). After filtering and washing with $CH_2Cl_2$ (5 mL×5 min×4), the resin was treated with 1M HCl (4 mL×1 min, than 8 mL×1.5 h), washed with $H_2O$ (5 mL×5 min×3), MeOH (5 mL×5 min×4) and dried in vacuo.

(13) O-{N-[L-serinyl-L-leucyl]-N-[(4-nitrophenylazo)-2-aminophenylethyl-N-ethyl]-L-tyrosinyl-L-valinyl}-N-(glutaryl-photolinker-PEGA-amide)-L-threonyl-L-arginine, Methyl Ester Prepared as for O-{N-[L-serinyl-L-leucyl]-N-[(4-nitrophenylazo)-2-aminophenylethyl-N-ethyl]-L-tyrosinyl-L-valinyl}-N-(glutaryl-photolinker-Tentaget-amide)-L-threonyl-L-arginine, methyl ester with 4-[4-{1-(9-fluorenylmethoxycarbonylamino)ethyl}-2-methoxy-5-nitrophenoxy]butan-PEGA-amide used in place of 4-[4-{1-(9-fluorenylmethoxycarbonylamino)ethyl} -2-methoxy-5-nitrophenoxy]butan-Tentagel-amide

(14) O-{N-[L-serinyl-L-leucyl]-N-[(4-nitrophenylazo)-2-aminophenylethyl-N-ethyl]-L-tyrosinyl-L-valinyl}-N-(glutaryl carboxamide)-L-threonyl-L-arginine, Methyl Ester A slurry of 3 mg of O-{N-[L-serinyl-L-leucyl]-N-[(4-nitrophenylazo)-2-aminophenylethyl-N-ethyl]-L-tyrosinyl-L-valinyl}-N-(glutaryl-photolinker-Tentagel-amide)-L-threonyl-L-arginine, methyl ester in 0.3 mL MeOH in a polypropylene ependorf tube was photolyzed at 366 nM for 5 h with a handheld uv-lamp. The red solution was analyzed by reverse phase HPLC and low res FAB and in both cases exhibited only one peak. Using the analytical reverse phase HPLC conditions described above, the acyclic ester's retention time is 9.8 min. Combining the photolysis products from several experiments yielded enough material for a proton NMR.

$^1$H NMR (300 MHz, $CD_3OD$) δ8.36 (d, J=9.1 Hz, 2), 7.95 (d, J=6.5 Hz, 2), 7.89 (d, J=7.2 Hz, 2), 7.08 (d, J=8.6 Hz, 1), 7.04 (d, J=8.8 Hz, 2), 6.95 (d, J=9.3 Hz, 1), 6.74 (d, J=5.1 Hz, 1), 6.71 (d, J=5.1 Hz, 1), 5.27 (m, 1), 4.65–4.45 (m, 2), 4.29 (m, 1), 4.01–3.90 (m, 2), 3.85–3.72 (m, 2), 3.70/3.68 (2s, 3), 3.67–3.45 (m, 7), 3.22–3.00 (m, 3), 2.39–2.20 (m, 5), 1.94–1.87 (m, 5), 1.33–1.17 (m, 8), 1.03–0.91 (m, 6), 0.85 (d, J=6.5 Hz, 3), 0.80 (d, J=6.6 Hz, 3); HRMS(FAB) Calcd for $C_{54}H_{77}N_{14}O_{13}$ (MH+): 1161.6057, found 1161.6070.

EXAMPLE 2

Solution-Phase Synthesis of Cyclic Depsipeptide

N-Glutaryl(2,4-dimethoxybenzylamide)-L-threonine

To a solution of 2.04 g of 2,4-dimethoxybenzylamine hydrochloride (10.0 mmol, 1.0 eq), 1.14 g of glutaric anhydride (10 mmol, 1.0 eq) and 3.5 mL of DIEA (20 mmol, 2.0 eq) in 100 mL $CH_2Cl_2$ was added 122 mg of DMAP (1 mmole, 0.1 eq). After stirring for 18 h, $H_2O$ (200 mL) and 1M HCl (20 mL) were added. The aqueous layer was further extracted with $CH_2Cl_2$ (3×100 mL), which yielded, after drying and evaporation, 2.82 g of the amide/acid product.

To a solution of 2.82 g of the above acid (10 mmol, 1.0 eq), 1.55 g of L-threonine, methyl ester (11.7 mmol, 1.2 eq), 1.42 g of HOBT (10.5 mmol, 1.1 eq) and 2.0 mL of DIEA (11.7 mmol, 1.2 eq) in 35 mL of DMF at −5° C. was added 2.23 g of EDC (11.7 mmol, 1.2 eq). After stirring for 14 h as the reaction warmed to room temperature, the solvent was removed in vacuo, and 1M HCl (500 mL) and $CH_2Cl_2$ (250 mL) were added. The aqueous layer was further extracted with $CH_2Cl_2$ (5×150 mL). The combined organic layer was dried, evaporated and purified by column chromatography, yielding 2.62 g of the Me-ester/amide product, (63% from 2,4 dimethoxybenzylamine hydrochloride).

To 446 mg of the above ester (1.13 mmol, 1.0 eq) in 60 mL 2:1 THF/MeOH was added 11 mL of 1M LiOH (11.0 mmol, 10.0 eq). After stirring for 50 min, 1M HCl (15 mL) was added portionwise. The mixture was concentrated to ca. 25 mL. The aqueous layer was extracted with CHCl3 (8×100 mL), dried and evaporated, yielding 295 mg of the acid product, (65%).

$^1$H NMR (300 MHz, $CDCl_3$) δ7.23 (bs, 1H), 7.10 (d, J=8.0 Hz, 1H), 6.67 (d, J=8.0 Hz, 1H), 6.41 (s, 1H), 6.40 (d, J=8.0 Hz, 1H), 4.54 (d, J=8.9 Hz, 1H), 4.36 (d, J=6.0 Hz, 1H), 4.29 (d, J=5.2 Hz, 2H), 3.76 (s, 6H), 2.21 (m, 4H), 1.91 (m, 2H), 1.16 (d, J=6.0 Hz, 3H).

(2) [N-(Carbobenzyloxy)—N8(4-methoxy-2,3,6-trimethyl benzenesulfonyl)]-L-arginyl-O-tert-butyl-L-serine, Trimethylsilylethyl Ester To a solution of 557 mg of trimethylsilylethanol (4.71 mmol, 1.0 eq), 1.39 g of (N-Cbz)(O-t-Bu)-L-serine (4.71 mmol, 1.0 eq), and 58 mg of DMAP (0.471 mmol, 0.1 eq) in 12 mL $CH_2Cl_2$ at 0° C. was added 993 mg EDC (5.18 mmol, 1.1 eq). After stirring for 24 h as the reaction warmed to room temperature, the solvent was removed in vacuo. The residue was partitioned between EtOAc (125 mL) and $H_2O$ (25 mL). The organic layer was washed with $NaHCO_3$(sat.) (2×75 mL), $H_2O$ (2×75 mL), dried and evaporated yielding 1.77 g of the ester, (95%). Rf=0.42, 5% MeOH/$CH_2Cl_2$.

A mixture of 1.73 g of the above ester (4.38 mmol, 1.0 eq), and 469 mg of 10% Pd/C (0.445 mmol, 0.1 eq) in 20 mL MeOH was hydrogenated under a balloon of H2 for 2 h, at which time filtering through a pad of Celite and removal of solvents yielded 1.05 g of the corresponding amine.

To a solution of 1.05 g of the above amine (4.02 mmol, 1.0 eq), 2.30 g of N-a-Cbz, N-g-Mtr arginine (4.43 mmol, 1.1 eq), 543 mg of HOBT (4.02 mmol, 1.0 eq) and 0.77 mL of DIEA (4.43 mmol, 1.1 eq) in 12 mL of DMF at −5° C. was added 846 mg of EDC (4.43 mmol, 1.1 eq). After stirring for 7 h as the reaction warmed to room temperature, the solvent was removed in vacuo, and $H_2O$ (1.6 L) and $CH_2Cl_2$ (200 mL) were added. The aqueous layer was further extracted with $CH_2Cl_2$ (4×200 mL). The combined organic layer was washed with 1M HCl (2×200 mL), $NaHCO_3$(sat.) (2×200 ml), NaCl(sat.) (1×200 mL) dried and evaporated yielding 2.94 g of the amide product (96% from the N-a-Cbz ester ).

$^1$H NMR (300 MHz, $CDCl_3$) δ7.33 (bs, 5H), 6.63 (d, J=8.1 Hz, 1H), 6.52 (s, 1H), 6.01 (a, 2H), 5.82 (bs, 1H), 5.63 (d, J=8.0 Hz, 1H), 5.08 (s, 2H), 4.64 (d, J=8.4 Hz, 1H), 4.31 (m, 1H), 4.24–4.20 (m, 2H), 3.84 (m, 1H), 3.81 (s, 3H), 3.54 (d, J=6.6 Hz, 1H), 3.21 (bs, 2H), 2.78 (s, 3H), 2.70 (s, 3H), 2.12 (s, 3H), 1.95 (m, 1H), 1.67 (m, 3H), 1.13 (s, 9H), 0.99 (t, J=9.6 Hz, 2H), 0.04 (s, 9H); $^{13}$C NMR (100 MHz, CDCl$_3$) δ171.7, 170.1, 162.4, 157.9, 156.0, 138.0, 136.0, 133.3, 128.0, 127.6, 127.4, 124.2, 111.3, 73.0, 66.4, 63.4, 61.3, 54.9, 54.1, 52.8, 40.1, 36.1, 31.0, 29.3, 26.8, 25.0, 23.7, 18.0, 16.9, 11.5,−1.9; HRMS(FAB) Calcd for C$_{36}$H$_{58}$N$_5$O$_9$SiS (MH+): 764.3714, found 764.3724; Rf: 0.73, 10% acetone/CH$_2$Cl$_2$ (3) N-[Glutaryl(2,4-dimethoxybenzylamide)]-L-threonyl-(N8—4-methoxy-2,3,6-trimethyl benzenesulfonyl)-L-arginyl—O-tert-butyl-L-serine, Trimethylsilylethyl Ester A mixture of 2.94 g of [N$_2$-(carbobenzyloxy)-N8(4-methoxy-2,3,6-trimethyl benzenesulfonyl)]-L-arginyl-0-tert-butyl-L-serine, trimethylsilylethyl ester (3.85 mmol, 1.0 eq), and 810 mg of 10% Pd/C (0.77 mmol, 0.2 eq) in 70 mL MeOH was hydrogenated under a balloon of H2 for 4 h, at which time filtering through a pad of Celite and removal of solvents yielded 2.42 g of the corresponding amine.

To a solution of 2.42 g of the above amine (3.85 mmol, 1.0 eq), 1.47 g of N-glutaryl(2,4-dimethoxybenzylamide)-L-threonine (3.85 mmol, 1.0 eq), 520 mg of HOBT (3.85 mmol, 1.0 eq) and 0.74 mL of DIEA (4.24 mmol, 1.1 eq) in 15 mL of DMF at −5° C. was added 810 mg of EDC (4.24 mmol, 1.1 eq). After stirring for 11 h as the reaction warmed to room temperature, the solvent was removed in vacuo, and H$_2$O (0.8 L) and CH$_2$Cl$_2$ (100 mL) were added. The aqueous layer was further extracted with CH$_2$Cl$_2$ (6×100 mL). The combined organic layer was washed with 1M HCl (2×250 mL), NaHCO$_3$(sat.) (2×250 ml), NaCl(sat.) (1×250 mL), dried and purified by column chromatography, yielding 2.50 g of the amide alcohol product (65% from the N-a—Cbz ester).:

$^1$H NMR (300 MHz, CDCl$_3$) δ7.46 (m, 11H), 7.10 (s, J=8.1 Hz, 11H), 6.99 (m, 2H), 6.55–6.48 (bs, 1H), 6.51 (s, 1H), 6.42–6.35 (m, 4H), 6.17 (bs, 1H), 4.57–4.54 (m, 1H), 4.42–4.29 (m, 2H), 4.29 (d, J=5.8 Hz, 2H), 4.21–4.16 (m, 2H), 3.81 (s, 3H), 3.79 (s, 3H), 3.78 (s, 3H), 3.78–3.75 (m, 1H), 3.52 (m, 1H), 3.21–3.10 (m, 2H), 2.6 (s, 3H), 2.61 (s, 3H), 2.31–2.21 (m, 4H), 2.11 (s, 3H), 1.96–1.91 (m, 4H), 1.68–1.53 (m, 3H), 1.16 (d, 6.4H, d), 1.11 (s, 9H), 1.01–0.95 (m, 2H), 0.04 (s, 9H); $^{13}$C NMR (100 MHz, CDCl$_3$) δ173.6, 172.6, 171.3, 170.8, 170.0, 159.8, 157.8, 156.1, 138.0, 135.9, 133.3, 129.2, 124.2, 118.2, 111.2, 103.5, 97.9, 77.2, 66.8, 63.3, 61.2, 57.9, 54.9, 54.8, 52.8, 40.2, 38.0, 34.7, 30.4, 29.1, 26.8, 24.9, 23.7, 21.6, 18.9, 17.9, 16.9, 13.1, 11.5, −2.0; HRMS(FAB) Calcd for C$_{46}$H$_{76}$N$_7$O$_{13}$SiS(MH+): 994.4980, found 994.4991; Rf: 0.39, 10% MeOH/CH$_2$Cl$_2$ (4) O-[N-(Carbobenzyloxy)-L-valinyl]-N-[glutaryl (2,4-dimethoxybenzylamide)]-L-threonyl-(N8–4-methoxy-2,3,6-trimnethyl benzenesulfonyl)-L-arginyl-(O-tert-butyl)-L-serine, Trimethylsilylethyl Ester To a solution of 2.50 g of N-[glutaryl(2,4-dimethoxybenzylamide)]-L-threonyl-(N8–4-methoxy-2,3,6-trimethyl benzenesulfonyl)-L-arginyl-O-tert-butyl-L-serine, trimethylsilylethyl ester (2.52 mmol, 1.0 eq), 1.90 g of N-a-Cbz-L-valine (7.55 mmol, 3.0 eq), and 31 mg of DMAP (0.25 mmol, 0.1 eq) in 20 mL CH$_2$Cl$_2$ at 0° C. was added 1.44 g of EDC (7.55 mmol, 3.0 eq). After stirring for 21 h as the reaction warmed to room temperature, the solvent was removed in vacuo. The residue was partitioned between EtOAc (350 mL) and H$_2$O (75 mL). The organic layer was washed with NaHCO$_3$(sat.) (2×150 mL), H20 (2×150 mL), dried and evaporated yielding 2.85 g of the ester, (92%).

$^1$H NMR (300 MHz, CDCl$_3$) δ7.41 (d, J=7.8 Hz, 1H), 7.29 (s, 5H), 7.08 (d, J=8.2 Hz, 1H), 6.83 (d, J=7.6 Hz, 1H), 6.58–6.50 (m, 1H), 6.53 (s, 1H), 6.40–6.36 (m, 2H), 6.22 (bs, 2H), 6.02 (m, 2H), 5.46 (m, 1H), 5.04 (dd, J=12.4, 3.0 Hz, 2H), 4.62 (m, 1H), 4.49 (m, 2H), 4.29 (m, 2H), 4.15 (m, 2H), 4.06 (m, 1H), 3.79 (s, 3H), 3.76 (s, 6H), 3.70 (m, 1H), 3.45 (m, 1H), 3.08 (m, 2H), 2.66 (s, 3H), 2.61 (m, 1H), 2.57 (s, 3H), 2.30 (m, 2H), 2.22 (m, 2H), 2.11 (m, 1H), 2.08 (s, 3H), 1.92 (m, 3H), 1.65 (m, 1H), 1.48 (m, 2H), 1.25 (d, J=6.3 Hz, 3H), 1.09 (s, 9H), 0.95 (m, 2H), 0.90 (dd, J=6.8, 3.0 Hz, 6H), 0.02 (s, 9H); $^{13}$C NMR (100 MHz, CDCl$_3$) δ173.3, 172.4, 171.1, 170.8, 170.0, 169.0, 160.0, 158.0, 156.6, 156.1, 138.2, 136.1, 135.9, 133.6, 129.3, 128.1, 127.7, 124.3, 118.4, 111.3, 103.6, 98.1, 77.2, 70.3, 66.6, 63.4, 61.3, 59.8, 56.1, 55.0, 52.8, 52.5, 40.3, 38.1, 34.8, 30.1, 29.6, 24.9, 23.8, 21.5, 18.7, 18.1, 17.8, 17.1, 16.7, 11.6, −1.9; HRMS (FAB) Calcd for C$_{59}$H$_{91}$N$_8$O$_{16}$SiS(MH+): 1127.6015, found 1127.6043; Rf: 0.28, 30% acetone/CH$_2$Cl$_2$ (5) O-[N-[(4-Nitrophenylazo)-2-aminophenylethyl-N-ethyl]-(O-tert-butyl)-L-tyrosinyl-L-valinyl]-N-[glutaryl(2,4-dimethoxybenzylamide)]-L-threonyl-(N8–4-methoxy-2,3,6-trimnethyl benzenesulfonyl)-L-arginyl-(O-tert-butyl)-L-serine, Trimethylsilylethyl Ester A mixture of 2.94 g of O-[N-(carbobenzyloxy)-L-valinyl]-N-fglutaryl(2,4-dimethoxybenzylamide)]-L-threonyl-(N8–4-methoxy-2,3,6-trimethyl benzenesulfonyl)-L-arginyl-(O-tert-butyl)-L-serine, trimethylsilylethyl ester (1.22 mmol, 1.0 eq), and 510 mg of 5% Pd/C (0.24 mimol, 0.2 eq) in 10 mL of MeOH were hydrogenated under a balloon of H2 for 3 h, at which time filtering through a pad of Celite and removal of solvents yielded 1.33 g of the corresponding amine.

To a solution of 1.33 g of the above amine (1.22 mmol, 1.0 eq), 910 mg of N-[(4-nitrophenylazo)-2-aminophenylethyl-N-ethyl], O-tert-butyl -L-tyrosine (1.71 mmol, 1.4 eq), 230 mg of HOBT (1.71 mmol, 1.4 eq) and 0.59 mL of DIEA (3.42 mmol, 2.8 eq) in 35 mL of DMF at −5° C. was added 326 mg of EDC (1.71 mmol, 1.1 eq). After stirring for 11 h as the reaction warmed to room temperature, the solvent was removed in vacuo, and H$_2$O (600 L) and CH$_2$Cl$_2$ (100 mL) were added. The aqueous layer was further extracted with CH$_2$Cl$_2$ (3×100 mL). The combined organic layer was washed with 1M HCl (2×150 mL), NaHCO$_3$(sat.) (1×250 ml), NaCl(sat.) (1×250 mL), dried, evaporated and purified by column chromatography yielding 862 mg of the amide product, (44%).

$^1$H NMR (300 MHz, CDCl$_3$) δ8.32 (d, J=9.1 Hz, 2H), 7.99 (d, J=9.0 Hz, 1H), 7.92 (d, J=9.1 Hz, 2H), 7.87 (d, J=9.1 Hz, 2H), 7.65 (d, J=8.5 Hz, 1H), 7.11 (d, J=7.8 Hz, 1H), 7.03 (d, J=9.4 Hz, 1H), 6.96 (d, J=8.4 Hz, 2H), 6.91 (d, J=8.4 Hz 2H), 6.67 (d, J=9.2 Hz, 2H), 6.61 (d, J=8.3 Hz, 1H), 6.49 (s, 1H), 6.43 (s, 2H), 6.41 (m, 1H), 6.33 (m, 1H), 6.12 (m, 1H), 5.58 (m, 1H), 4.69 (dd, J=9.0, 3.3 Hz, 1H), 4.52–4.20 (m, 5H), 4.18 (m, 2H), 3.79 (s, 6H), 3.78 (s, 3H), 3.75 (m, 1H), 3.60–3.15 (m, 7H), 3.05 (m, 1H), 2.80 (m, 2H), 2.69 (s, 3H), 2.66 (m, 2H), 2.63 (s, 3H), 2.40–2.20 (m, 4H), 2.09 (s, 3H), 2.01–1.40 (m, 7H), 1.30 (s, 9H), 1.29 (d, J=6.7 Hz, 3H), 1.11 (s, 12H), 0.97 (m, 2H), 0.88 (d, J=6.7 Hz, 3H), 0.83 (d, J=6.8 Hz, 3H); $^{13}$C NMR (100 MHz, CDCl$_3$) δ174.1, 173.3, 172.4, 170.7, 170.4, 169.9, 168.9, 160.0, 158.0, 157.9, 156.5, 156.1, 154.1, 151.3, 146.8, 143.3, 138.1, 136.0, 133.8, 131.0, 129.3, 129.2, 125.9, 124.3, 124.0, 122.2, 118.3, 111.3, 111.2, 103.7, 98.1, 78.0, 77.2, 73.0, 70.9, 69.2, 63.7, 63.4, 61.3, 56.4, 56.2, 55.0, 54.9, 53.7, 52.7, 52.6, 49.7, 46.1, 44.8, 38.1, 34.7, 34.5, 31.4, 30.3, 29.1, 29.0, 28.5, 26.9, 24.4, 23.8, 21.5, 18.8, 18.1, 17.0, 16.9, 16.2, 11.7, –1.9; HRMS(FAB) Calcd for $C_{80}H_{118}N_{13}O_{18}$ (MH+): 1608.8176, found 1608.8208; Rf: 0.52, 30% acetone/$CH_2Cl_2$ (6) O-{N-[(9-Fluorenylmethoxycarbonyl)-leucyl]-N-[(4-nitrophenylazo)-2-aminophenylethyl-N-ethyl]-(O-tert-butyl)-L-tyrosinyl-L-valinyl]}-N-[glutaryl(2, 4-dinethoxybenzylaniide)]-L-threonyl-(N8–4-methoxy-2,3,6-trimethyl benzenesulfonyl)-L-arginyl-(O-tert-butyl)-L-serine, Trimethylsilylethyl Ester A solution of 770 mg of O-[N-[(4-nitrophenylazo)-2-aminophenylethyl-N-ethyl]-(O-tert-butyl)-L-tyrosinyl-L-valinyl] -N- [glutaryl(2,4-dimethoxybenzylamide)]-L-threonyl-(N8-4methoxy-2,3,6-trimethyl benzenesulfonyl)-L-arginyl-(O-tert-butyl)-L-serine, trimethylsilylethyl ester (0.63 mmol, 1.0 eq), 4.25 g of FmocLeu acid fluoride (11.98 mmol, 25.0 eq) and 2.46 g of 2,6-di-t-butyl-4-methylpyridine (11.98 nunol, 25.0 eq) in 6 mL DMF was stirred under $N_2$ for 4 days. After removal of the DMF in vacuo, column chromatography and size exclusion chromatography yielded 368 mg of the amide product (40%, 62% BRSM ) and 90 mg of recovered SM amine.

$^1$H NMR (300 MHz, $CDCl_3$) δ8.30 (dd, J=8.9, 6.5 Hz, 2H), 7.95 (m, 1H), 7.91 (m, 4H), 7.72 (m, 2H), 7.57 (m, 2H), 7.41–7.26 (m, 4H), 7.07–6.89 (m, 8H), 6.76 (m, 1H), 6.69 (m, 1H), 6.49 (s, 1H), 6.40–6.36 (m, 5H), 5.50 (bs, 1H), 5.43 (m, 1H), 5.31 (d, J=5.2 Hz, 1H), 4.93 (bs, 1H), 4.63–4.33 (m, 5H), 4.32–4.02 (m, 7H), 3.79 (s, 3H), 3.77 (s, 6H), 3.78–3.75 (m, 1H), 3.52–3.48 (m, 4H), 3.32 (m, 1H), 3.30–3.00 (m, 4H), 2.68 (s, 3H), 2.61 (s, 3H), 2.40–1.8 (m, 11H), 2.09 (s, 3H), 1.80–1.40 (m, 5H), 1.33–1.11 (m, 24H), 1.00–0.73 (m, 14H), 0.03 (2s, 9H); HRMS(FAB) Calcd for $C_{101}H_{139}N_{14}O_{21}SSi$(MH+): 1943.9782, found 1943.9729; Rf: 0.72, 30% acetone/$CH_2Cl_2$ (7) Cyclo-O-{N-leucyl-N-[(4-nitrophenylazo)-2-aminophenylethyl-N-ethyl]-(O-tert-butyl)-L-tyrosinyl-L-valinyl]}-N-[glutaryl(2,4-dimethoxybenzylamide)]-L-threonyl-(N8–4-methoxy-2,3,6-trimethyl benzenesulfonyl)-L-arginyl-(O-tert-butyl)-L-serinyl A solution of 368 mg of O-{N-[(9-fluorenylmethoxycarbonyl)-leucyl]-N-[(4-nitrophenylazo)-2-aminophenylethyl-N-ethyl]-(O-tert-butyl)-L-tyrosinyl-L-valinyl}-N-[glutaryl(2,4-dimethoxybenzylamide)]-L-threonyl-(N8–4-methoxy-2,3,6-trimethyl benzenesulfonyl)-L-arginyl-(O-tert-butyl)-L-serine, trimethylsilylethyl ester (0.19 mmol, 1.0 eq) and 0.75 mL of piperidine (7.6 mmol, 40 eq) in 15 ml of $CH_2Cl_2$ were stirred for 1.5 h. After removal of volatiles in vacuo and purification by size exclusion chromatography, 305 mg of the corresponding amine was obtained, (93%).

To a solution of 342 mg of the above amine (0.2 mmol, 1.0 eq) in 5 mL of DMF was added 1.0 ml of 1.0M TBAF/THF (1.0 mmol, 5.0 eq). After stirring for 1.5 h, EtOAc (250 mL) was added. The organic layer was washed with $H_2O$ (250 mL), NaCl(sat.) (250 mL), dried, and purified by size exclusion chromatography with LH-20, yielding 330 mg of the corresponding crude amino acid. Rf=0.34, 10% MeOH/$CH_2Cl_2$.

To a solution of the above amine, 107 mg of HOBT (0.80 mmol, 4.0 eq) and 24 mL of N-methyl morpholine (0.22 mmol, 1.1 eq) in 200 mL THF was added 152 mg of EDC (0.80 mmol, 4.0 eq). After stirring for 24 h, the reaction mixture was partioned between EtOAc (500 mL) and NaCl (sat.) (500 mL). The organic layer was dried, evaporated and purified by column chromatography, yielding 205 mg of the protected macrocyclic product, (64%).

$^1$H NMR (300 MHz, $CDCl_3$) δ8.31 (d, J=9.0 Hz, 2H), 7.92 (m, 4H), 7.83 (d, J=8.9 Hz, 1H), 7.60 (d, J=8.2 Hz, 1H), 7.16–6.83 (m, 9H), 6.56 (d, J=7.9 Hz, 1H), 6.50 (m, 2H), 6.41 (s, 1H), 6.41–6.35 (m, 3H), 5.58 (m, 1H), 5.46 (m, 1H), 5.01 (bs, 1H), 4.73–4.20 (m, 9H), 3.80–3.72 (m, 10H), 3.60–3.40 (m, 4H), 3.40–2.90 (m, 5H), 2.66 (s, 3H), 2.59 (s, 3H), 2.75–2.55 (m, 2H), 2.50–2.11 (m, 2H), 2.10 (s, 3H), 1.92 (m, 2H), 1.80–1.35 (m, 5H), 1.30 (s, 9H), 1.32–1.19 (m, 15H), 0.97–0.64 (m, 12H); HRMS(FAB) Calcd for $C_{81}H_{115}N_{14}O_{18}S$(MH+): 1603.8241, found 1603.8235; Rf: 0.32, 7.5% MeOH/$CH_2Cl_2$ (8) Cyclo-O-{N-leucyl-N-[(4-nitrophenylazo)-2-aminophenylethyl-N-ethyl]-L-tyrosinyl-L-valinyl]}-N-[glutaryl(2,4-dimethoxybenzylamide)]-L-threonyl-L-arginyl-L-serinyl, 2a SEQ ID NO: 2

To a solution of 97 mg of cyclo-O-{N-leucyl-N-[(4-nitrophenylazo)-2-aminophenylethyl-N-ethyl]-(O-tert-butyl)-L-tyrosinyl-L-valinyl) }-N-[glutaryl(2,4-dimethoxybenzylamide)]-L-threonyl-(N8-4-methoxy-2,3,6-trimethyl benzenesulfonyl)-L-arginyl-(O-tert-butyl)-L-serinyl (0.06 mmol, 1.0 eq) in 1.85 mL of $CH_2Cl_2$ was added 0.05 mL of $H_2O$ and 41 mg of 2,3-dichloro-5,6-dicyano-1, 4-benzoquinone (0.18 mmol, 3.0 eq). After stirring for 6.5 h, the mixture was partitioned between $CH_2Cl_2$ (40 mL) and Na2CO3(sat.)(40 mL). The aqueous layer was extracted once more with $CH_2Cl_2$ (40 mL) and the organic layer was dried and evaporated yielding 47 mg of the crude primary amide.

The crude amide was treated with 10 mL of an 85% TFA/5% phenol/5% thiophenol/5% thioanisole cleavage cocktail for 7 h. Upon removal of volatiles in vacuo, hexanes (5×100 mL) was added and decanted. Further purification by preparative reverse phase HPLC yielded 18 mg of the fully deprotected cyclic depsipeptide, (44%). Using the analytical reverse phase HPLC conditions described above, the cyclic depsipeptide's retention time is 10.9 min.

$^1$H NMR (300 MHz, $CD_3OD$) δ8.61 (d, J=8.0 Hz, 1H), 8.52 (d, J=8.1 Hz, 1), 8.43 (d, J=8.0 Hz, 1), 8.36 (d, J=9.1 Hz, 2), 7.95 (d, J=9.1 Hz, 2), 7.90 (d, J=9.2 Hz, 2), 7.86 (d, J=8.0 Hz, 2), 7.72 (d, J=8.4 Hz, 1), 7.37 (m, 1), 7.05 (d, J=9.4 Hz, 2), 7.00 (d, J=8.5 Hz, 2), 6.80 (d, J=9.1 Hz, 1), 6.71 (d, J=8.5 Hz, 2), 5.60–5.40 (m, 2), 4.60–4.35 (m, 5), 3.82 (d, J=5.8 Hz, 1), 3.70–3.50 (m, 2), 3,42 (m, 1), 3.38 (m, 1), 3.15 (m, 1), 3.08 (m, 1), 3.00–2.90 (m, 1), 2.41–2.33 (m, 3), 2.28–2.05 (m, 4), 1.96–1.86 (m, 3), 1.77–1.45 (m, 7), 1.36 (d, J=6.6 Hz, 3), 1.33–1.21 (m, 4), 1.17–1.14 (m, 1), 1.02 (d, J=6.9 Hz, 3), 0.94 (m, 2), 0.87 (d, J=2.8 Hz, 3), 0.85 (d, J=2.9 Hz, 3), 0.68 (d, J=6.6 Hz, 3), 0.58–0.48 (m, 1); HRMS(FAB) Calcd for $C_{54}H_{77}N_{14}O_{13}$ (MH+): 1129.5794, found 1129.5787;

EXAMPLE 3

Trypsin Assays

All assays were performed at 37° C. on a Kontron Uvikon 860 UV-Vis spectrophotmeter. The forward reaction rate was measured by monitoring the absorbance change at 410 nm of the para-nitroanilide produced ( e=8800 $M^{-1}$ $cm^{-1}$ at 410 nm) at 30 sec intervals for 15 min. The concentrations of inhibitor solutions were determined spectrophotometrically from Disperse Red 1's extinction coefficient of 15,562 $M^{-1}$ $cm^{-1}$ at 490 nm. The assay mixtures contained inhibitor, L-BAPNA, 50 mL of DMSO, 200 mL of a 0.001 M HCl trypsin solution, and 750 mL of 100 mM TRIS/10 mM $CaCl_2$ solution (pH=8.0). For the assay of the cyclic inhibitor, the following concentrations were employed: [trypsin]=22 nM, [L-BAPNA]=540 mM, [cyclic inhibitor]= 4.5, 3.4, 2.3, 1.1, and 0.6 mM. Trypsin was added last to the assay solutions and the kinetic data was immediately collected. For the assay of the acyclic inhibitor, the following concentrations were employed: [trypsin]=87 nM, [L-BAPNA]=540 mM, [acyclic inhibitor]=17.2, 8.6, 4.3, 2.2, and 1.1 mM. The acyclic inhibitor was produced in situ by adding trypsin to the cyclic inhibitor in the assay medium lacking the L-BAPNA. After incubating the solution for 25 min at 37° C., the L-BAPNA in DMSO was added, and the kinetic data was immediately collected. Inhibition constants ($K_i$'s) were determined from the slope of the $V_0/v$ vs. [inhibitor] plots where the slope=$1/K_i(1 +[L-BAPNA]/K_m)$ and $K_m$=2.0 +/−0.3 mM, $V_0$ =rate in the absence of inhibitor and v=rate in the presence of inhibitor. The $K_m$ of L-BAPNA in 5% DMSO, 100 mM TRIS/10 mM $CaCl_2$ (pH=8.0) was calculated to be 2.0 +/−0.3 mM by both Lineweaver-Burke and non-linear regression analysis of the initial rates using the Enzyme Kinetics program. The following concentrations were employed in the $K_m$ determination: [trypsin]=43 nM, [L-BAPNA]=3.0, 2.5, 2.0, 1.5, 1.0 and 0.5 mM. The inhibition constant $K_{i=230\ nM\ determined\ for\ the\ macrocyclic\ analog\ was}$ the average value of 3 separate determinations.

All publications and patent applications mentioned in this specification are herein incorporated by reference to the same extent as if each individual publication or patent application was specifically and individually indicated to be incorporated by reference.

The invention now being fully described, it will be apparent to one of ordinary art that many changes and modifications can be made thereto without departing pirit or scope of the appended claims.

What is claimed is:

1. A method for detecting enzyme-catalyzed cyclization of acyclic amino compounds, comprising;

a) contacting a composition suspected of containing peptidase with an acyclic amino compound of Formula I:

$$NH_2—R^1—X—R^2—C(O)—Y$$

wherein:
C(O)Y represents a carboxylic acid or an ester or amide that can be acylated or hydrolyzed by said peptidase $R^1$ and $R^2$ each comprises one or more amino acid residues connected by covalent bonds and forming a structure that acts as a substrate of said peptidase, in which
one of said amino acid residues in $R^1$ is linked to a dye molecule or a resin, and
one of said amino acid residues in $R^2$ is linked to a resin or to a dye molecule, respectively, to provide a dye molecule attached on one side of X in said formula and a resin attached on the other side of X in said formula; and
X is a group cleavable under reaction conditions that do not cleave an amide said group comprising an ester group, a disulfide group, a —CH(OH)—CH(OH)— group, or a carbonate group;

b) contacting the product of step a) with an X-cleaving agent under said reaction conditions that do not cleave an amide;

c) isolating the resin; and d) determining the presence or absence of the dye molecule on the isolated resin; wherein cyclization of said acyclic amino compound and presence of said peptidase is detected by retention of the dye molecule on the resin.

2. The method of claim 1, wherein $R^1$ and $R^2$ each represent 1–20 amino acid residues.

3. The method of claim 1, wherein Y is —$OR^3$, —$SR^3$, or —$NHR^3$, in which $R^3$ is hydrogen, alkyl, cycloalkyl, aryl, or heteroaryl.

4. The method of claim 3, wherein $R^1$ and $R^2$ combined represent between 2 and 30 amino acid residues.

5. The method of claim 1, wherein the peptidase is chosen from trypsin, thrombin, CMV protease, pepsin, renin, HIV protease, cathepsin, matrilysin, stromelysin, angiotensin converting enzyme, caspase, and HCV protease.

6. The method of claim 1, wherein the X-cleaving agent is chosen from a base, a reducing agent and an oxidizing agent.

7. The method of claim 1, wherein the resin product of step b) is isolated by filtration and washing with a solvent.

8. The method of claim 7, wherein the solvent is a mixture of methanol and water.

9. The method of claim 1, wherein X is an ester linkage of formula —C(O)—O—$R^3$—, in which —O—$R^3$— represents a link to a hydroxy group of threonine, serine, or hydroxyproline.

10. The method of claim 1, wherein an $NH_2$ group of a threonine, serine, or hydroxyproline residue in $R^1$ or $R^2$ is linked to said resin by —C(O)—$(CH_2)_3$—C(O)—NH—L, wherein L represents a resin linker.

11. The method of claim 9, wherein X is cleaved by a base selected from the group consisting of compounds having a formula ROM, wherein R is hydrogen, methyl, or ethyl, and M is sodium, potassium, or lithium.

12. The method of claim 1, wherein the dye molecule is attached to an N atom of an amino acid residue.

13. The method of claim 12, wherein the amino acid residue is tyrosine and the dye is Disperse Red 1.

14. The method of claim 13, wherein the resin is linked to $R^1$ or $R^2$ by —C(O)—$(CH2)_3$—C(O)—NH—L, where L represents a resin linker.

15. The method of claim 1, wherein the amino acid residues represented by $R^1$ and $R^2$ are chosen from serine, threonine, allo-threonine, glutamine, lysine, glycine, valine, histidine, homoserine, isoserine, β-alanine, 1-amino-1-carboxycyclopentane, leucine, proline, O-benzylserine, 3-(aminomethyl)benzoic acid, tyrosine, aspartic acid, alanine, 2-carboxypiperidine, 3-carboxypiperidine, 3-(aminomethyl)benzoic acid, arginine, phenylalanine, and alanine units.

16. A method of discovering a peptidase inhibitor of Formula II from a collection of potential peptidase inhibitors, comprising:

a) contacting a peptidase with an acyclic amino compound of Formula I:

$$NH_2—R^1—X—R^2—C(O)—Y$$

wherein:
C(O)Y represents a carboxylic acid or an ester or amide that can be acylated or hydrolyzed by said peptidase $R^1$ and $R^2$ each comprises one or more amino acid residues connected by covalent bonds, in which
one of said amino acid residues in $R^1$ is linked to a dye molecule or a resin, and
one of said amino acid residues in $R^2$ is linked to a resin or to a dye molecule, respectively, to provide a dye molecule attached on one side of X in said formula and a resin attached on the other side of X in said formula; and
X is a group cleavable under reaction conditions that do not cleave an amide said group comprising an ester group, a disulfide group a —CH(OH)—CH(OH)— group, or a carbonate group;

b) contacting the product of step a) with an X-cleaving agent under said reaction conditions that do not cleave an amide;

c) isolating the resin; and d) determining the presence or absence of the dye molecule on the isolated resin;

wherein ability of said compound of Formula I to act as an inhibitor of said peptidase is detected by retention of the dye molecule on the resin, thereby identifying as a peptidase inhibitor a compound of Formula II:

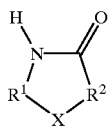

where $R^1$, $R^2$, and X are as defined above.

17. The method of claim 16, wherein $R^1$ and $R^2$ each represent 1–20 amino acid residues.

18. The method of claim 16, wherein Y is —$OR^3$, —$SR^3$, or —$NHR^3$, in which $R^3$ is hydrogen, alkyl, cycloalkyl, aryl, or heteroaryl.

19. The method of claim 16, wherein $R^1$ and $R^2$ combined represent between 2 and 30 amino acid residues.

20. The method of claim 16, wherein the peptidase is chosen from trypsin, thrombin, CMV protease, pepsin, renin, HIV prolease, cathepsin, matrilysin, stromelysin, angiotensin converting enzyme, caspase, and HCV protease.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<221> NAME/KEY: SITE
<222> LOCATION: (3)
<223> OTHER INFORMATION: linked to dye molecule
<220> FEATURE:
<221> NAME/KEY: SITE
<222> LOCATION: (4)..(5)
<223> OTHER INFORMATION: Thr is acylated on oxygen with Val
<220> FEATURE:
<221> NAME/KEY: SITE
<222> LOCATION: (5)
<223> OTHER INFORMATION: modified on N and connected to solid support:
      (NH-C(O)-(CH2)3CONH-L), where L is hydrogen or a
      resin plus linker
<220> FEATURE:
<221> NAME/KEY: SITE
<222> LOCATION: (6)
<223> OTHER INFORMATION: linked to OR, where R is hydrogen or methyl
<220> FEATURE:
<223> OTHER INFORMATION: Description of Artificial Sequence: synthesized
      enzyme substrate

<400> SEQUENCE: 1

Ser Leu Tyr Val Thr Arg
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: synthesized
      enzyme substrate
<220> FEATURE:
<221> NAME/KEY: CHAIN
<222> LOCATION: (1)..(6)
<223> OTHER INFORMATION: Oxygen of serinyl cyclized to leucyl
<220> FEATURE:
<221> NAME/KEY: SITE
<222> LOCATION: (2)
<223> OTHER INFORMATION: modified with
      (4-nitrophenylazo)-2-aminophenylethyl-N-ethyl
<220> FEATURE:
<221> NAME/KEY: SITE
```

```
<222> LOCATION: (4)
<223> OTHER INFORMATION: modified with glutaryl(2,4-dimethoxy-
      benzylamide)
<220> FEATURE:
<221> NAME/KEY: SITE
<222> LOCATION: (3)..(4)
<223> OTHER INFORMATION: Thr is acylated on oxygen with Val

<400> SEQUENCE: 2

Leu Tyr Val Thr Arg Ser
 1               5
```